(12) United States Patent
Fukushima

(10) Patent No.: US 12,154,795 B2
(45) Date of Patent: Nov. 26, 2024

(54) CONTAINER STORAGE FACILITY

(71) Applicant: Daifuku Co., Ltd., Osaka (JP)

(72) Inventor: Hidemoto Fukushima, Komaki (JP)

(73) Assignee: Daifuku Co., Ltd., Osaka (JP)

( * ) Notice: Subject to any disclaimer, the term of this patent is extended or adjusted under 35 U.S.C. 154(b) by 275 days.

(21) Appl. No.: 17/983,648

(22) Filed: Nov. 9, 2022

(65) Prior Publication Data

US 2023/0141291 A1 May 11, 2023

(30) Foreign Application Priority Data

Nov. 10, 2021 (JP) ................................. 2021-183244

(51) Int. Cl.
| | |
|---|---|
| *F24F 11/89* | (2018.01) |
| *F24F 11/52* | (2018.01) |
| *G01J 5/00* | (2022.01) |
| *G01N 33/00* | (2006.01) |
| *H01L 21/67* | (2006.01) |
| *F24F 110/76* | (2018.01) |
| *F24F 120/10* | (2018.01) |

(52) U.S. Cl.
CPC ........ *H01L 21/67017* (2013.01); *F24F 11/52* (2018.01); *F24F 11/89* (2018.01); *G01J 5/0025* (2013.01); *G01N 33/0036* (2013.01); *F24F 2110/76* (2018.01); *F24F 2120/10* (2018.01)

(58) Field of Classification Search
CPC ................................................ H01L 21/67017

USPC ....................................................... 73/31.05
See application file for complete search history.

(56) References Cited

U.S. PATENT DOCUMENTS

| | | | |
|---|---|---|---|
| 9,779,973 B2 | 10/2017 | Murata et al. | |
| 2015/0000759 A1* | 1/2015 | Takahara | H01L 21/67769 |
| | | | 137/15.04 |
| 2017/0256428 A1* | 9/2017 | Kawamura | H01L 21/67775 |

FOREIGN PATENT DOCUMENTS

WO          2015045582 A1     4/2015

* cited by examiner

*Primary Examiner* — Walter L Lindsay, Jr.
*Assistant Examiner* — Philip T Fadul
(74) *Attorney, Agent, or Firm* — The Webb Law Firm

(57) ABSTRACT

A container storage facility includes a container storage rack including a plurality of container placement sections that are next to each other in a first direction, and further includes a first sensor group of oxygen concentration sensors next to each other in the first direction on a first side of the containers in a second direction; a second sensor group of oxygen concentration sensors next to each other in the first direction on a second side of the containers in the second direction; a third sensor group of oxygen concentration sensors next to each other in the first direction at positions further toward the first side in the second direction than the first sensor group; and a fourth sensor group of oxygen concentration sensors next to each other in the first direction at positions further toward the second side in the second direction than the second sensor group.

5 Claims, 9 Drawing Sheets

CONTAINER STORAGE FACILITY

CROSS-REFERENCE TO RELATED APPLICATION

This application claims priority to Japanese Patent Application No. 2021-183244 filed Nov. 10, 2021, the disclosure of which is hereby incorporated by reference in its entirety.

BACKGROUND OF THE INVENTION

1. Field of the Invention

The present invention relates to a container storage facility including a container storage rack including a plurality of container placement sections on each of which a container is placeable, and an inactive gas supply apparatus configured to supply an inactive gas to each of the containers placed on the container placement sections.

2. Description of the Related Art

An example of such a container storage facility is disclosed in WO 2015/045582 (Patent Document 1). In the following, the reference numerals and the names of the components disclosed in Patent Document 1 are cited in the description of the related art.

A purging device described in Patent Document 1 is provided in a stocker (2) installed in a clean room. An internal space (6) of the stocker (2) is divided into a work area (12) and a non-work area (14). A partition (30) for restricting the entry of a purge gas from the non-work area (14) into the work area (12) is placed at the boundary between the work area (12) and the non-work area (14). The purging device stops purging in the work area (12) when a worker enters the internal space (6). The purging device monitors the oxygen concentration in the work area (12), and, if a detection result of the oxygen concentration in the work area (12), which is a result obtained from an oxygen concentration sensor (54), is less than or equal to a predetermined value, stops the supply of the purge gas also in the non-work area (14).

SUMMARY OF THE INVENTION

According to the technique described in Patent Document 1, when a worker enters the internal space, purging in the work area is stopped to ensure the safety of the worker. Furthermore, if the oxygen concentration in the work area is less than or equal to the predetermined value, purging in the non-work area is stopped, thus restoring the oxygen concentration in the work area. Incidentally, for example, some container storage racks are suspended from and supported by a ceiling, and include a plurality of container placement sections next to each other. In such a container storage rack, there may be an area in which the oxygen concentration is locally reduced according to the extent of leakage of an inactive gas from the containers. In such a case, a worker cannot enter the area in which the oxygen concentration is reduced. For this reason, in order for the worker to perform work on such a container storage rack, it is necessary to appropriately detect the presence of an area in which the oxygen concentration is locally reduced. However, Patent Document 1 does not disclose detecting a local reduction in the oxygen concentration around such a container storage rack suspended from the ceiling.

Therefore, it is desirable to realize a container storage facility capable of appropriately detecting the oxygen concentration around a container storage rack that is suspended from and supported by a ceiling and that includes a plurality of container placement sections next to each other.

In view of the foregoing, a characteristic feature of a container storage facility lies in a container storage facility including:
  a container storage rack including a plurality of container placement sections on each of which a container is placeable; and
  an inactive gas supply apparatus configured to supply an inactive gas to each of the containers placed on the container placement sections,
wherein the container storage rack is configured to be suspended from and supported by a ceiling, and the plurality of container placement sections are next to each other in a first direction extending in a horizontal direction, and,
the container storage facility further includes:
  a first sensor group including a plurality of oxygen concentration sensors at an overlapping height and next to each other in the first direction on a first side of the containers in a second direction orthogonal to the first direction as viewed in a vertical direction, the overlapping height being a position overlapping the containers placed on the container placement sections;
  a second sensor group including a plurality of oxygen concentration sensors at the overlapping height and next to each other in the first direction on a second side of the containers in the second direction;
  a third sensor group including a plurality of oxygen concentration sensors at a first predetermined height and next to each other in the first direction at positions further toward the first side in the second direction than the first sensor group, the first predetermined height being lower than the overlapping height; and
  a fourth sensor group including a plurality of oxygen concentration sensors at a second predetermined height and next to each other in the first direction at positions further toward the second side in the second direction than the second sensor group, the second predetermined height being lower than the overlapping height.

In a container storage facility including a container storage rack including a plurality of container placement sections on each of which a container is placeable, and an inactive gas supply apparatus configured to supply an inactive gas to each of the containers placed on the container placement sections, the oxygen concentration may be locally reduced according to the extent of leakage of the inactive gas from the containers. In this case, a worker cannot enter the area in which the oxygen concentration is reduced. In particular, with a container storage rack that is suspended from and supported by a ceiling, the oxygen concentration may be locally reduced in the vicinity of the head of a worker approaching the container storage rack. In such a case, it is necessary to appropriately detect the reduction, and alert the worker or the like. With this configuration, it is possible to appropriately detect oxygen concentrations around a container storage rack that is suspended from and supported by a ceiling, wherein the head of a worker is assumed to approach the container storage rack from below.

Further features and advantages of the technique according to the present disclosure will become apparent from the following description of illustrative and non-limiting embodiments with reference to the drawings.

DETAILED DESCRIPTION OF THE INVENTION

An embodiment of the container storage facility will be described with reference to the drawings. The present embodiment will be described, taking, as an example, a case where the container storage facility is installed in a down flow-type clean room in which clean air flows downward from the ceiling side toward the floor side.

Figure 1:
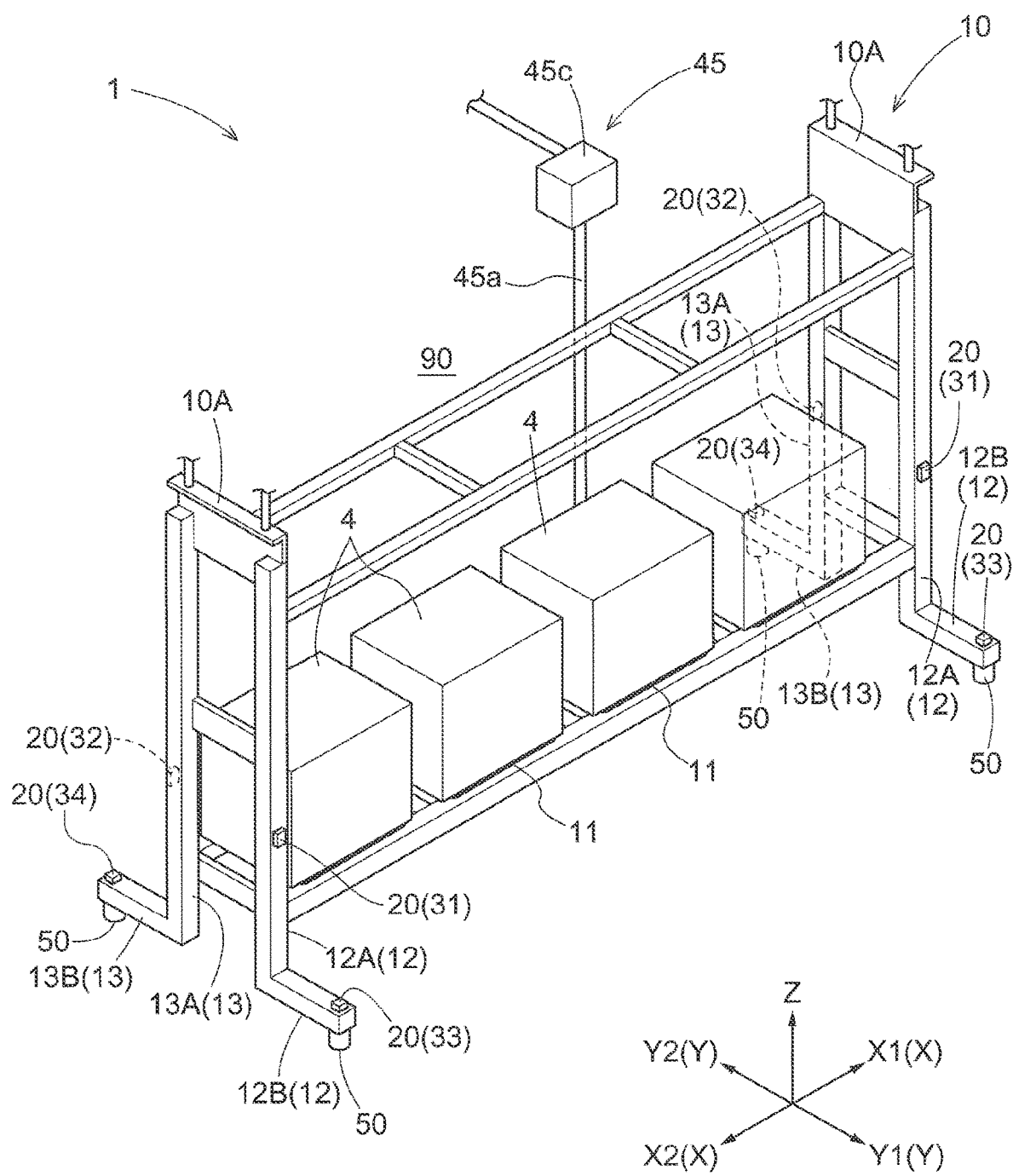
FIG. 1 is a perspective view of a container storage facility according to an embodiment of the present disclosure.

As shown in FIG. 1, a container storage facility 1 includes a container storage rack 10 and an inactive gas supply apparatus 45. The container storage rack 10 is a rack that stores containers 4. In the present embodiment, the container storage rack 10 is illustrated as an open rack having no peripheral wall portion disposed therearound. The container storage rack 10 includes a plurality of container placement sections 11 on each of which a container 4 is placeable. Also, an inactive gas is supplied from the inactive gas supply apparatus 45 to each of the containers 4 placed on the container placement sections 11.

Here, in the present embodiment, a first direction X is a specific direction (in the present embodiment, the longitudinal direction of the container storage rack 10, which is a direction that extends in a horizontal direction) extending in the horizontal direction, a second direction Y is a direction extending orthogonal to the first direction X as viewed in a vertical direction, and a third direction Z is a direction extending in the vertical direction, which extends orthogonal to both the first direction X and the second direction Y. Also, the present embodiment is described with a first direction-first side X1 being one side in the first direction X, and a first direction-second side X2 being the other side in the first direction X. Also, the present embodiment is described with a second direction-first side Y1 being one side in the second direction Y, and a second direction-second side Y2 being the other side in the second direction Y.

The container storage rack 10 is configured to be suspended from and supported by a ceiling. The container storage rack 10 includes a pair of suspension parts 10A spaced apart in the first direction X. The container storage rack 10 is suspended from the ceiling by coupling the suspension parts 10A to supporters (not shown) provided on the ceiling of a clean room, for example. The pair of suspension parts 10A are disposed above the container placement sections 11 of the container storage rack 10.

Figure 6:
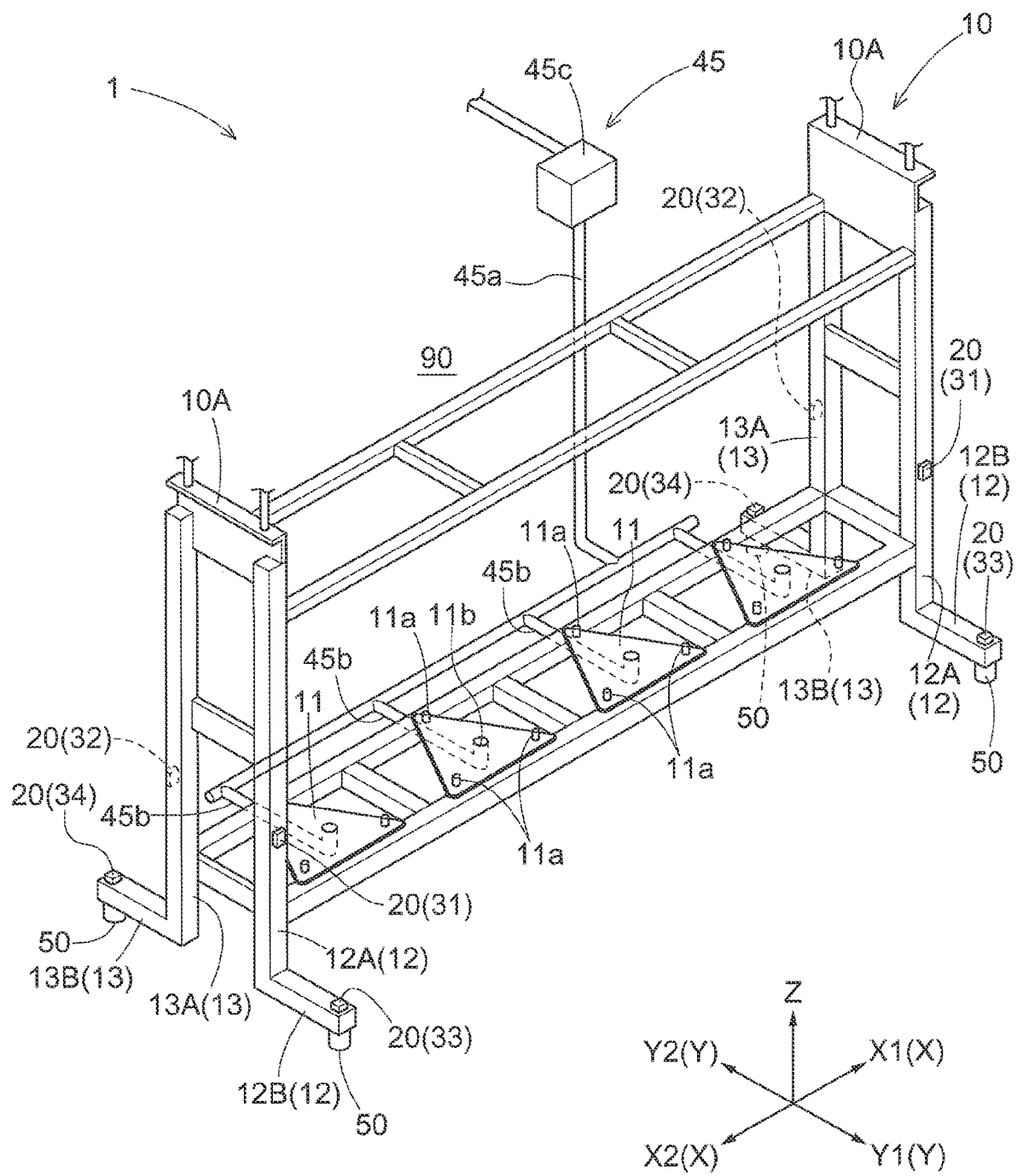
FIG. 6 is a diagram showing a layout of human detection sensors.

In the present embodiment, as shown in FIG. 6, positioning pins 11a for positioning a container 4 by engaging with a bottom of portion of the container 4 are disposed on each of the container placement sections 11. Each of the container placement sections 11 is also provided with a gas supply part 11b for supplying an inactive gas to the container 4 that is connected to a connection port provided at the bottom portion of the container 4. A plurality of container placement sections 11 are next to each other in the first direction X. The container storage rack 10 according to the present embodiment includes four container placement sections 11. Thus, one container storage rack 10 is capable of storing a maximum of four containers 4.

In the present embodiment, each container 4 can be sealed in such a manner that its internal space is air-tightly sealed. For example, a semiconductor substrate, a reticle substrate, or the like can be housed in the container 4. In the present embodiment, the container 4 includes a body part, and a cover part configured to be detachable from the body part, and the container 4 is configured such that the internal space of the container 4 is in an air-tight state while the cover part is attached to the body part.

The inactive gas supply apparatus 45 is configured to supply an inactive gas via a supply part (not shown) into the containers 4 placed on the plurality of container placement sections 11. The inactive gas is a gas that has low reactivity with an object housed in the container 4 (a gas that produces substantially no problematic chemical reaction). In the present embodiment, nitrogen gas is used as the inactive gas. As the inactive gas, carbon dioxide may be used in place of nitrogen gas, or a noble gas such as helium, neon, argon, krypton, xenon, or radon may be used.

The inactive gas supply apparatus 45 includes a first pipe 45a connected to a supply source of the inactive gas, and second pipes 45b that connect the first pipe 45a and the containers 4 to one another. In the present embodiment, the first pipe 45a extends in the third direction Z, and the second pipes 45b branch from the first pipe 45a and extend in the first direction X and the second direction Y. Also, each of the second pipes 45b is connected to the gas supply part 11b provided on the corresponding placement part 11.

The inactive gas supply apparatus 45 also includes a flow rate adjustment device 45c capable of adjusting the flow rate of the inactive gas in the first pipe 45a and the second pipes 45b. The supply flow rate of the inactive gas supplied to each container 4 can be adjusted by the flow rate adjustment device 45c adjusting the flow rate of the inactive gas in the first pipe 45a and the second pipes 45b. In FIG. 1, the flow rate adjustment device 45c is provided on the first pipe 45a. However, the flow rate adjustment device 45c may be provided on the second pipes 45b. The inactive gas from the inactive gas supply apparatus 45 is supplied to each of the containers 4, thus making the pressure in the container 4 positive. When the internal pressure of the container 4 becomes greater than or equal to a certain pressure, part of the inactive gas inside the container 4 is discharged to the outside of the container 4 (a storage space 90 of the container storage facility 1 in the clean room). The air in the storage space 90, which is air containing the inactive gas discharged from the container 4, flows downward from the ceiling side toward the floor side in response to the circulation of clean air in the clean room.

The container storage facility 1 includes a plurality of oxygen concentration sensors 20. The oxygen concentration sensors 20 detect the oxygen concentration at their respective positions. The oxygen concentration sensors 20 may be any type of oxygen concentration sensor, including, but not limited to, zirconia, magnetic, laser spectroscopic, and electrode type oxygen concentration sensors. In the present embodiment, the container storage facility 1 includes a first sensor group 31, a second sensor group 32, a third sensor group 33, and a fourth sensor group 34, each of which includes a plurality of oxygen concentration sensors 20.

Figure 2:
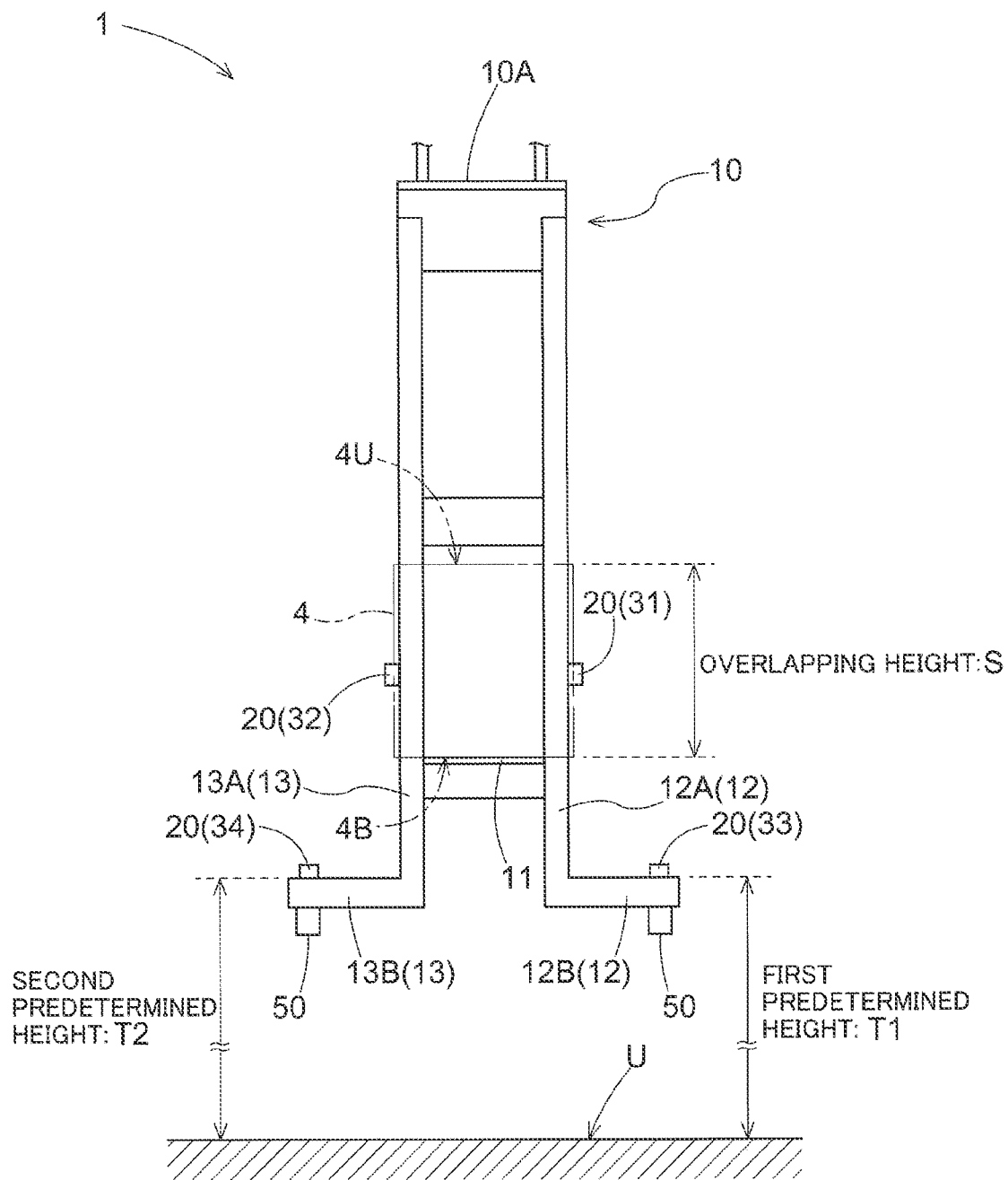
FIG. 2 shows a container storage rack as viewed from a first direction-second side.

The first sensor group 31 includes a plurality of oxygen concentration sensors 20 at an overlapping height S and next to each other in the first direction X on the second direction-first side Y1 of the containers 4. FIG. 2 shows the container storage rack 10 as viewed from the first direction-second side X2. The overlapping height S is a position overlapping the containers 4 placed on the container placement sections 11 when the container storage rack 10 is viewed in the first direction X, as shown in FIG. 2. That is, the overlapping height S is the height, in the third direction Z, from a lower end 4B of the containers 4 placed on the container placement sections 11 to an upper end 4U thereof. In the present embodiment, the second direction-first side Y1 corresponds to the right side of left and right sides in the second direction Y when the container storage rack 10 is viewed toward the first direction-first side X1 as shown in FIG. 2, for example. The expression "next to each other in the first direction X" means that the plurality of oxygen concentration sensors 20 constituting the first sensor group 31 are aligned in the first direction X. Accordingly, the first sensor group 31 is disposed on the right side in the second direction Y relative to the container storage rack 10 within a range of the height in the third direction Z from the lower end 4B to the upper end 4U of the containers 4 placed on the container placement sections 11 when the container storage rack 10 is viewed in the first direction X, and when the container storage rack 10 is viewed toward the first direction-first side X1.

Figure 3:
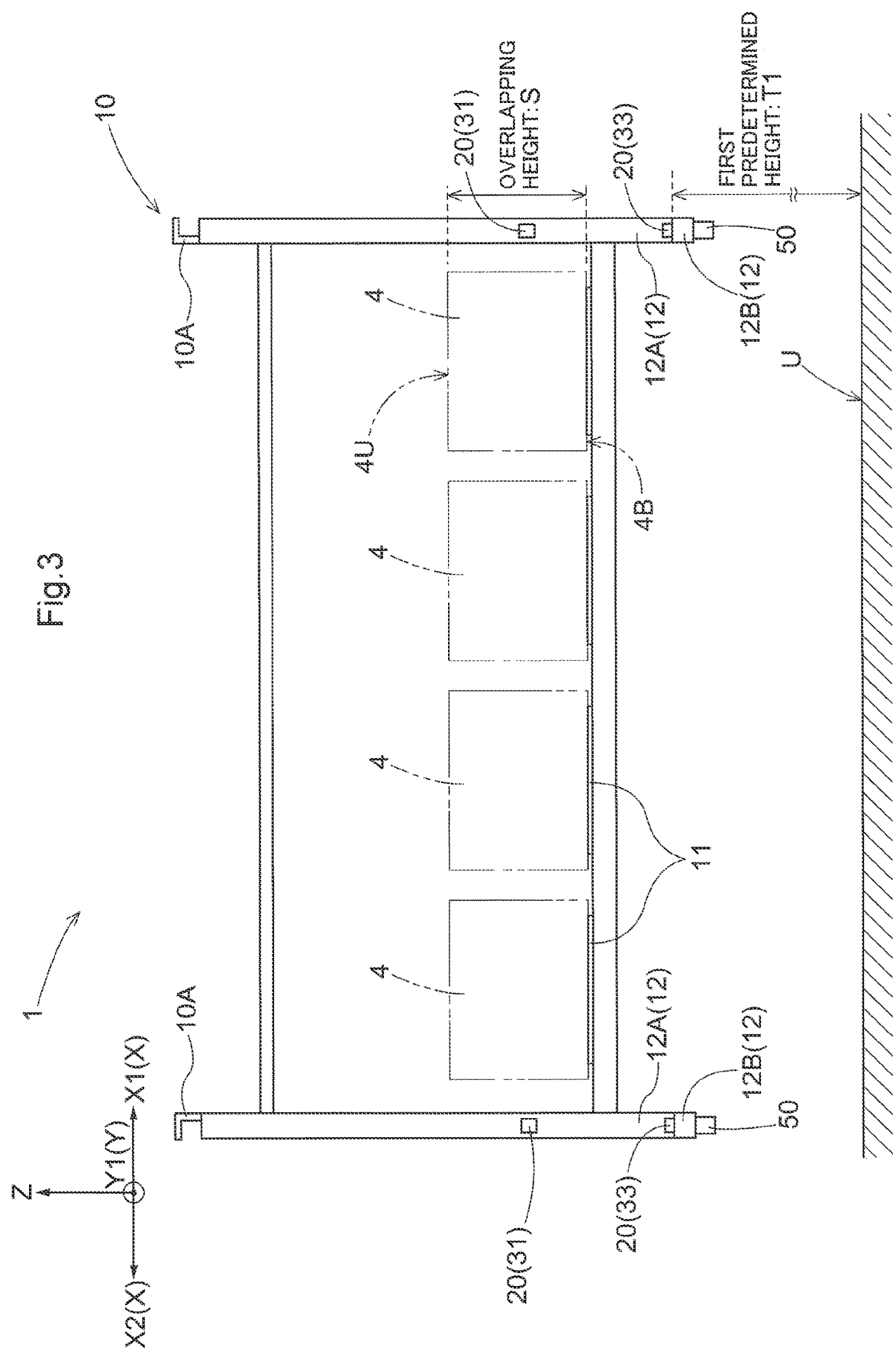
FIG. 3 shows the container storage rack as viewed from a second direction-first side.

Here, FIG. 3 shows the container storage rack 10 as viewed from the second direction-first side Y1. In the present embodiment, as shown in FIG. 3, the first sensor group 31 includes two oxygen concentration sensors 20 next to each other in the first direction X. In the present example, as shown in FIG. 3, the oxygen concentration sensors 20 constituting the first sensor group 31 are respectively disposed at an end portion of the container storage rack 10 on the first direction-first side X1 and an end portion thereof on the first direction-second side X2. Note that the first sensor group 31 may include three or more oxygen concentration sensors 20 next to each other in the first direction X. In this case, the distance in the first direction X between two adjacent oxygen concentration sensors 20 of the first sensor group 31 is shorter than that in the example shown in FIG. 3.

The second sensor group 32 includes a plurality of oxygen concentration sensors 20 at the overlapping height S and next to each other in the first direction X on the second direction-second side Y2 of the containers 4. In the present embodiment, the second direction-second side Y2 corresponds to the left side of left and right sides in the second direction Y when the container storage rack 10 is viewed toward the first direction-first side X1 as shown in FIG. 2, for example. Accordingly, the second sensor group 32 is disposed on the left side in the second direction Y relative to the container storage rack 10 within a range of the height in the third direction Z from the lower end 4B to the upper end 4U of the containers 4 placed on the container placement sections 11 when the container storage rack 10 is viewed in the first direction X, and when the container storage rack 10 is viewed toward the first direction-first side X1. In this manner, the first sensor group 31 and the second sensor group 32 are disposed on opposite sides in the second direction Y with the container storage rack 10 interposed therebetween.

Figure 4:
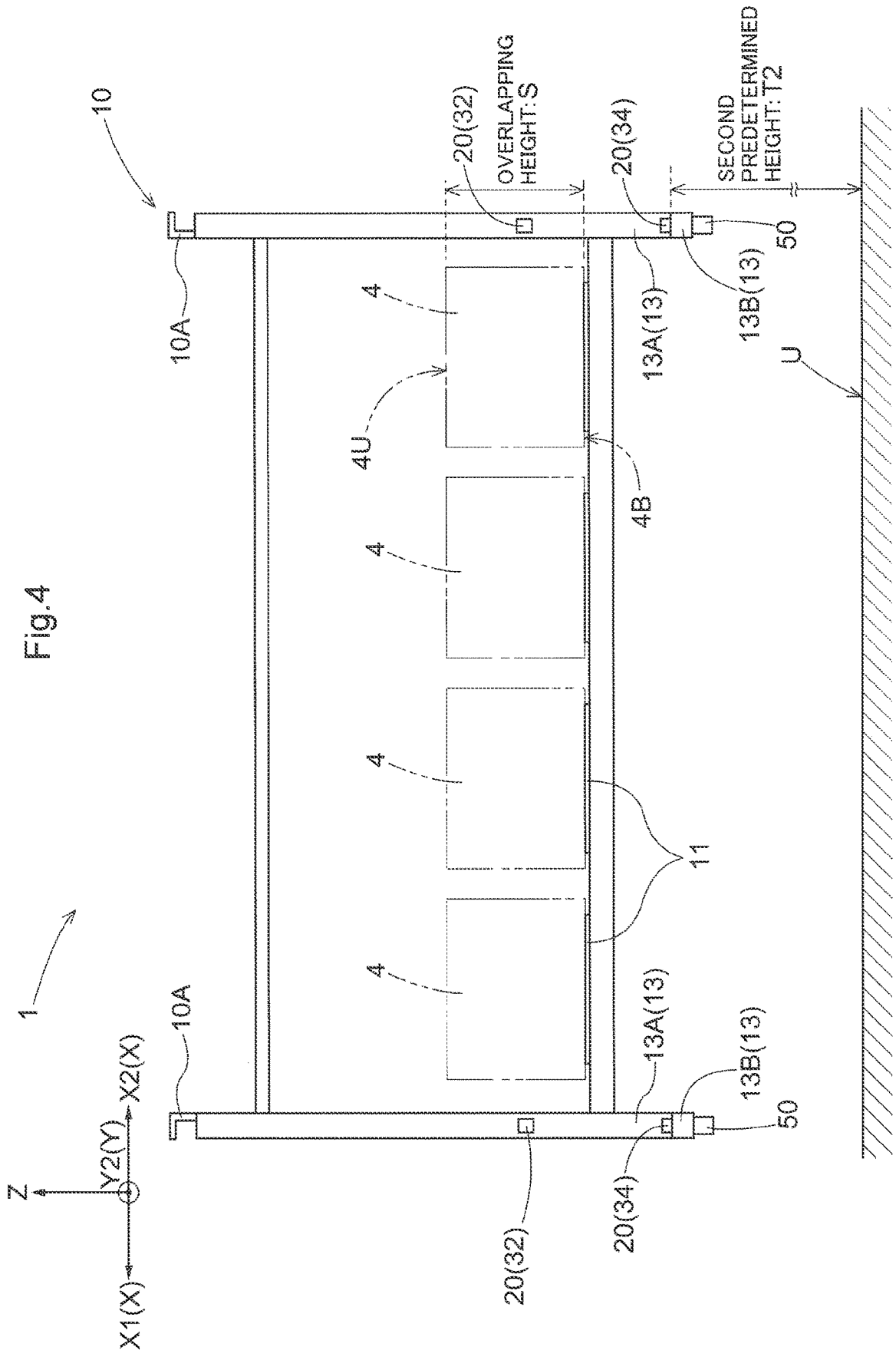
FIG. 4 shows the container storage rack as viewed from a second direction-second side.

Here, FIG. 4 shows the container storage rack 10 as viewed from the second direction-second side Y2. In the present embodiment, as shown in FIG. 4, the second sensor group 32 includes two oxygen concentration sensors 20 next to each other in the first direction X. In the present example, as shown in FIG. 4, the oxygen concentration sensors 20 constituting the second sensor group 32 are respectively disposed at an end portion of the container storage rack 10 on the first direction-first side X1 side and an end portion thereof on the first direction-second side X2. Note that the second sensor group 32 may include three or more oxygen concentration sensors 20 next to each other in the first direction X. In this case, the distance in the first direction X between two adjacent oxygen concentration sensors 20 of the second sensor group 32 is shorter than that in the example shown in FIG. 4.

The third sensor group 33 includes a plurality of oxygen concentration sensors 20 at a first predetermined height T1 and next to each other in the first direction X at positions further toward the second direction-first side Y1 than the first sensor group 31, the first predetermined height T1 being lower than the overlapping height S. As shown in FIG. 2, the first predetermined height T1 is a height in the third direction Z that is lower than the lower end 4B of the containers 4 placed on the container placement sections 11. In the present embodiment, the first predetermined height T1 is set to a height such that the distance in the third direction Z from the lower end 4B of the containers 4 is less than or equal to a length corresponding to the overlapping height S. In the illustrated example, the first predetermined height T1 is set as the height from a floor surface U. The expression "positions further toward the second direction-first side Y1 than the first sensor group 31" refers to a region further distanced from a central portion of the container storage rack 10 in the second direction Y than the first sensor group 31, as shown in FIG. 2. Accordingly, the third sensor group 33 is disposed at the first predetermined height T1 that is lower than the overlapping height S in the third direction Z, at a position further spaced apart from the central portion of the container storage rack 10 in the second direction Y than the first sensor group 31 when the container storage rack 10 is viewed in the first direction X.

Here, in the present embodiment, as shown in FIG. 3, the third sensor group 33 includes two oxygen concentration sensors 20 next to each other in the first direction X. In the present example, as shown in FIG. 3, the oxygen concentration sensors 20 constituting the third sensor group 33 are respectively disposed at an end portion of the container storage rack 10 on the first direction-first side X1 and an end portion thereof on the first direction-second side X2. In the present example, support members 12 are provided on the second direction-first side Y1 of the container storage rack 10, respectively at an end portion of the container storage rack 10 on the first direction-first side X1, and at an end portion thereof on the first direction-second side X2. Also, each of the oxygen concentration sensors 20 constituting the third sensor group 33 is supported on the container storage rack 10 using the corresponding support member 12. In the present example, each of the support members 12 includes a first extension part 12A extending downward in the third direction Z on the second direction-first side Y1 of the container storage rack 10, from an end portion on the first direction-first side X1 of the container storage rack 10 or an end portion on the first direction-second side X2 thereof, and a second extension part 12B extending toward the second direction-first side Y1 from a lower end portion of the first extension part 12A. In the present example, each of the oxygen concentration sensors 20 constituting the third sensor group 33 is disposed at a distal end portion of the corresponding second extension part 12B on the second direction-first side Y1.

The fourth sensor group 34 includes a plurality of oxygen concentration sensors 20 at a second predetermined height T2 and next to each other in the first direction X at positions further toward the second direction-second side Y2 than the second sensor group 32, the second predetermined height T2 being lower than the overlapping height S. As shown in FIG. 2, the second predetermined height T2 is a height in the third direction Z that is lower than the lower end 4B of the containers 4 placed on the container placement sections 11. In the present embodiment, the second predetermined height T2 is set to a height such that the distance in the third direction Z from the lower end 4B of the containers 4 is less than or equal to a length corresponding to the overlapping height S. In the illustrated example, the second predetermined height T2 is set as the height from the floor surface U. The expression "further toward the second direction-second side Y2 than the second sensor group 32" refers to a region further spaced apart from the central portion of the container storage rack 10 in the second direction Y than the second sensor group 32, as shown in FIG. 2. Accordingly, the fourth sensor group 34 is disposed at the second predetermined height T2 that is lower than the overlapping height S in the third direction Z, at a position further spaced apart from the central portion of the container storage rack 10 in the second direction Y than the second sensor group 32 when the container storage rack 10 is viewed in the first direction X.

Here, in the present embodiment, as shown in FIG. 4, the fourth sensor group 34 includes two oxygen concentration sensors 20 next to each other in the first direction X. In the present example, as shown in FIG. 4, the oxygen concentration sensors 20 constituting the fourth sensor group 34 are respectively disposed at an end portion of the container storage rack 10 on the first direction-first side X1 and an end portion thereof on the first direction-second side X2. In the present example, support members 13 are provided on the second direction-second side Y2 of the container storage rack 10, respectively at an end portion of the container storage rack 10 on the first direction-first side X1, and at an end portion thereof on the first direction-second side X2. Also, each of the oxygen concentration sensors 20 constituting the fourth sensor group 34 is supported on the container storage rack 10 using the corresponding support members 13. In the present example, each of the support members 13 includes a first extension part 13A extending downward in the third direction Z on the second direction-second side Y2 of the container storage rack 10, from an end portion on the first direction-first side X1 of the container storage rack 10 or an end portion on the first direction-second side X2 thereof, and a second extension part 13B extending toward the second direction-second side Y2 from a lower end portion of the first extension part 13A. In the present example, each of the oxygen concentration sensors 20 constituting the fourth sensor group 34 is disposed at a distal end portion of the corresponding second extension part 13B on the second direction-second side Y2.

In the present embodiment, the first predetermined height T1 and the second predetermined height T2 are set to the same height. With this configuration, the first sensor group 31, the second sensor group 32, the third sensor group 33, and the fourth sensor group 34 are disposed in a trapezoidal shape when the container storage rack 10 is viewed in the first direction X. This facilitates appropriate detection of a reduction in oxygen concentration caused by an inactive gas that is discharged from the containers 4, carried by an air flow moving from the ceiling portion of the clean room to the floor portion thereof, and diffused in a direction toward the floor surface U.

Note that the first predetermined height T1 and the second predetermined height T2 may be different from each other. In this case, the first predetermined height T1 may be higher than the second predetermined height T2, or the second predetermined height T2 may be higher than the first predetermined height T1.

Figure 5:
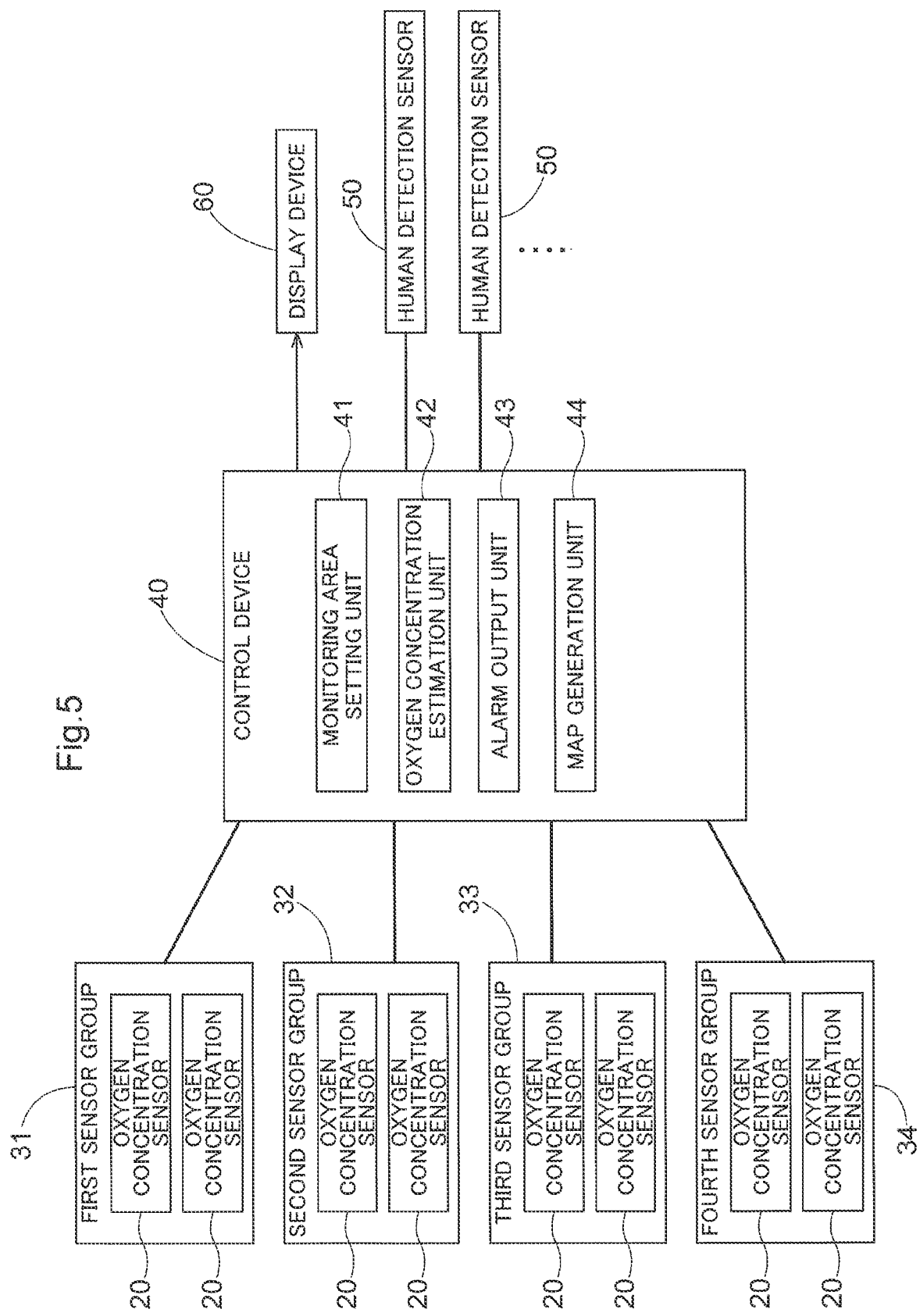
FIG. 5 is a block diagram showing functional units relating to alarm output performed by a control device.

Here, in the present embodiment, the container storage facility 1 includes a control device 40 and at least one human detection sensor 50, and the control device 40 is configured to output an alarm according to detection results of the oxygen concentration sensors 20 and a detection result of the human detection sensor 50. FIG. 5 is a block diagram showing functional units relating to alarm output performed by the control device 40.

The control device 40 includes a monitoring area setting unit 41, an oxygen concentration estimation unit 42, an alarm output unit 43, and a map generation unit 44. Each of these functional units is constructed by hardware or software, or both hardware and software, with a CPU serving as the core member.

The human detection sensor 50 detects the presence of a person in a detection range. In the present example, the human detection sensor 50 detects infrared radiation within a preset detection range, and detects the presence of a person in the detection range based on a change in the infrared radiation. Naturally, a human detection sensor configured to emit ultrasonic waves to the surrounding region thereof, and detect the presence of a person based on reflected ultrasonic waves can be used as the human detection sensor 50, for example. In the present embodiment, a plurality of human detection sensors 50 are distributed around the container storage rack 10.

FIG. 6 shows an example of the layout of the oxygen concentration sensors 20 and the human detection sensors 50 according to the present embodiment. In the present example, as shown in FIG. 6, eight oxygen concentration sensors 20 are provided on the container storage rack 10. In the present example, four human detection sensors 50 are provided at lower portions of the container storage rack 10. In the present embodiment, each of the human detection sensors 50 is disposed in such a manner as to detect a range below the container placement section 11 as a detection range. In the present example, a human detection sensor 50 is provided facing the floor surface U side, at a distal end portion of the second extension part 12B of each of the two support members 12 on which the oxygen concentration sensors 20 of the third sensor group 33 are provided, and a distal end portion of the second extension part 13B of each of the two support members 13 on which the oxygen concentration sensors 20 of the fourth sensor group 34 are provided. Accordingly, each of the human detection sensors 50 in the present example is disposed in such a manner as to detect, as a detection range, a range below the container placement sections 11 and overlapping the container storage rack 10 as viewed in the third direction Z (as viewed in the vertical direction).

Figure 7:
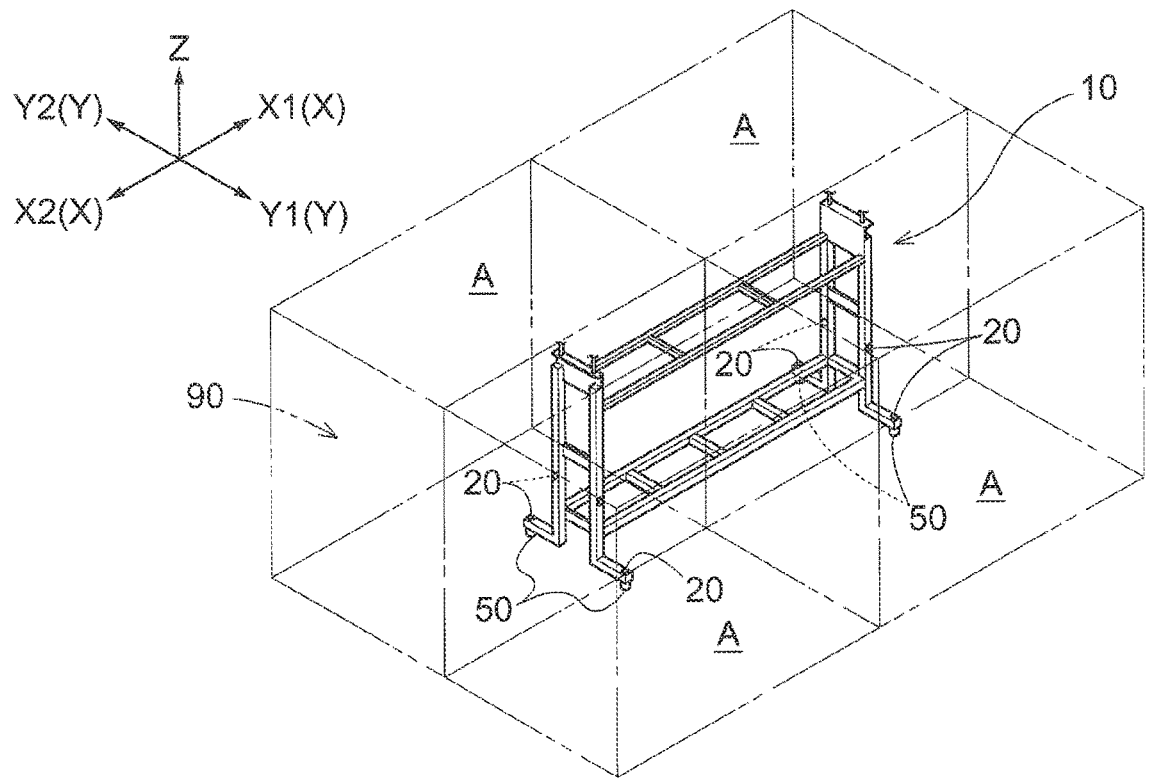
FIG. 7 shows an example of monitoring area settings.

The monitoring area setting unit 41 sets monitoring areas A obtained by dividing a space including the container storage rack 10, the first sensor group 31, the second sensor group 32, the third sensor group 33, and the fourth sensor group 34 into a plurality of segments. The expression "obtained by dividing a space . . . into a plurality of segments" means dividing the space into a plurality of segments of a predetermined size. In the present embodiment, the monitoring area setting unit 41 divides a space (hereinafter referred to as a "storage rack-peripheral space") including all of the container storage rack 10, the first sensor group 31, the second sensor group 32, the third sensor group 33, and the fourth sensor group 34 into a plurality of segments of a predetermined size. Each of the divided areas is regarded as a monitoring area A. In the present example, as shown in FIG. 7, the monitoring area setting unit 41 divides the storage rack-peripheral space into two segments in the first direction X, and two segments in the second direction Y. In the present example, there is one segment in the third direction Z. Accordingly, four monitoring areas A are set in the example shown in FIG. 7.

Figure 8:
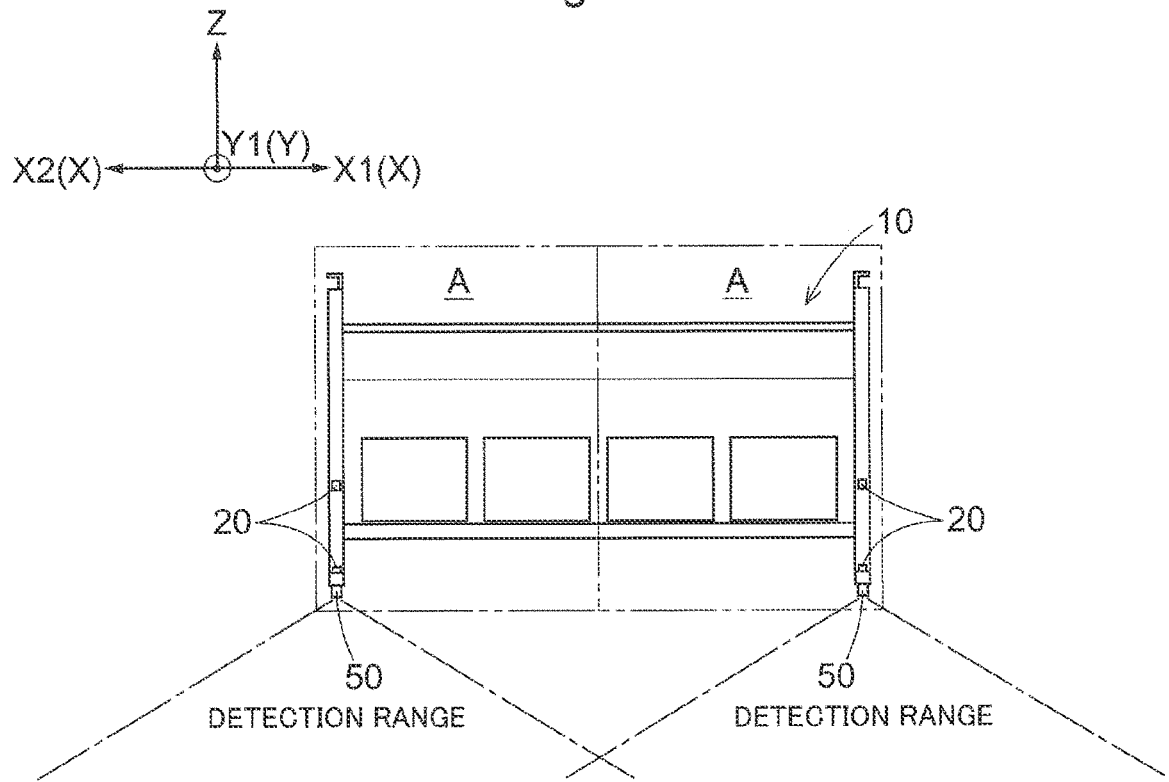
FIG. 8 is a diagram showing an example of detection ranges detected by the human detection sensor.

The human detection sensors 50 are configured to detect the presence of a person attempting to enter their respective monitoring areas A. As shown in FIG. 8, in the present embodiment, each of the human detection sensors 50 is disposed in such a manner as to detect a range below the container placement sections 11 of the container storage rack 10 as a detection range. This allows the human detection sensor 50 to detect a person approaching the container placement section 11 from below. Here, the container storage rack 10 is suspended from a ceiling. Accordingly, in most cases, a person attempting to enter a monitoring area A approaches the container placement section 11 from below. Therefore, it can be determined that a person detected by the human detection sensor 50 is a person attempting to enter the monitoring area A. In the present embodiment, a plurality of human detection sensors 50 are disposed in one-to-one correspondence with the plurality of monitoring areas A. That is, each of the human detection sensors 50 is disposed in such a manner as to detect a range below the corresponding one of the plurality of monitoring areas A as a detection range. In the present example, one human detection sensor 50 is disposed in each of the four monitoring areas A. Also, each of the human detection sensors 50 is configured to detect a person approaching the corresponding monitoring area A from below.

The oxygen concentration estimation unit 42 estimates the oxygen concentration of each of the plurality of monitoring areas A based on the detection value of each of the plurality of oxygen concentration sensors 20. The plurality of oxygen concentration sensors 20 are the two oxygen concentration sensors 20 constituting the first sensor group 31, the two oxygen concentration sensors 20 constituting the second sensor group 32, the two oxygen concentration sensors 20 constituting the third sensor group 33, and the two oxygen concentration sensors 20 constituting the fourth sensor group 34. Detection values are transmitted to the oxygen concentration estimation unit 42 from the oxygen concentration sensors 20. In the present example, the detection values of the oxygen concentration sensors 20 are transmitted in real time, or at a certain time interval, to the oxygen concentration estimation unit 42. Based on the transmitted detection values of the oxygen concentration sensors 20, the oxygen concentration estimation unit 42 estimates the oxygen concentrations in the plurality of monitoring areas A. In the present example, each of the plurality of monitoring areas A is set so as to include two oxygen concentration sensors 20. A minimum value or an average value of the detection values of the two oxygen concentrations may be used for each of the monitoring areas A. For example, detection values of two oxygen concentration sensors 20 that are adjacent to each other may be used to calculate a gradient (concentration gradient) of the oxygen concentration, and the oxygen concentration may be estimated for each of the plurality of monitoring areas based on the calculated result.

The alarm output unit 43 outputs an alarm in response to at least one of the monitoring areas being a low-oxygen concentration area A1 (see FIG. 9) in which the estimated oxygen concentration is less than or equal to a predetermined determination threshold, and the corresponding human detection sensor 50 detecting a person attempting to enter the low-oxygen concentration area A1. The estimated oxygen concentration is an oxygen concentration estimated by the oxygen concentration estimation unit 42 for each of the monitoring areas. The determination threshold is, for example, a lower limit value defining the oxygen concentration at which a worker can perform work in the container storage facility 1 without issue. Detection results are transmitted to the alarm output unit 43 from the human detection sensors 50.

The alarm output unit 43 determines, in real time, whether or not the oxygen concentration estimated by the oxygen concentration estimation unit 42 for each of the monitoring areas is less than or equal to the determination threshold. Then, in this determination, if there is at least one monitoring area A in which the oxygen concentration is less than or equal to the determination threshold, the alarm output unit 43 determines the monitoring area A as being the low-oxygen concentration area A1, and, if a detection result of the corresponding human detection sensor 50 indicates that a person is attempting to enter the low-oxygen concentration area A1 in which the oxygen concentration is less than or equal to the determination threshold, an alarm is output. Here, the alarm may be an alarm indicating, to a person attempting to enter the low-oxygen concentration area A1, that the oxygen concentration in the monitoring area A is reduced, or may be an alarm prompting the person to move away from the monitoring area A. For example, the container storage rack 10 or the clean room may be provided with a speaker, and the alarm may be output from the speaker. The alarm may be output from a terminal carried by a manager of the clean room. Such an alarm may be output using audio, image display, character display, or the like. Alternatively, the alarm may be a simple buzzing sound.

The oxygen concentration estimation unit 42 may be configured to, based on detection values of all the oxygen concentration sensors 20 constituting the first sensor group 31, the second sensor group 32, the third sensor group 33, and the fourth sensor group 34, estimate a minimum value of the oxygen concentration of each of the plurality of monitoring areas A through spatial interpolation. That is, for example, rather than estimating the oxygen concentration for each of the monitoring areas A, detection values of a plurality of oxygen concentration sensors 20 that are adjacent to each other are used to estimate a gradient (concentration gradient) of the oxygen concentration in each location, and the oxygen concentration distribution in each of the plurality of monitoring areas A is estimated based on the estimated value. Also, the oxygen concentration estimation unit 42 estimates the value of the lowest oxygen concentration in the thus estimated oxygen concentration distribution in each of the monitoring areas A as the minimum value of the oxygen concentration of the monitoring area A. With such an oxygen concentration estimation method using spatial interpolation, it is possible to appropriately estimate oxygen concentrations, not only in the above-described configuration in which two oxygen concentration sensors 20 are included in each of the plurality of monitoring areas A, but also in a configuration in which a monitoring area A including the oxygen concentration sensors 20 and a monitoring area A not including the oxygen concentration sensors 20 are present, and a configuration in which one, or three or more oxygen concentration sensors 20 are included in one monitoring area A.

The alarm output unit 43 may be configured to determine a monitoring area A in which the minimum value of the oxygen concentration estimated by the oxygen concentration estimation unit 42 is less than or equal to the determination threshold as being a low-oxygen concentration area A1, and output an alarm in response to the corresponding human detection sensor 50 detecting a person attempting to enter such a low-oxygen concentration area A1.

In the case where the container storage facility 1 includes a display device 60, the map generation unit 44 may display, on the display device 60, the oxygen concentration estimated for each of the plurality of monitoring areas A as an oxygen concentration map associated with the location of the container storage rack 10. The oxygen concentration estimated for each of the plurality of monitoring areas A is an oxygen concentration estimated by the oxygen concentration estimation unit 42. Accordingly, the map generation unit 44 may obtain an estimation result obtained as a result of the oxygen concentration estimation unit 42 estimating the oxygen concentrations. The oxygen concentration map associated with the location of the container storage rack 10 is a map indicating oxygen concentrations in which each of the monitoring areas A for which the oxygen concentration has been estimated is associated with an image obtained by imaging the container storage rack 10. Specifically, a model of the clean room in which the container storage rack 10 is disposed is created, and the map indicates a plurality of oxygen concentrations that are divided in such a manner as to correspond to the monitoring areas A in the model. The map generation unit 44 may generate such an oxygen concentration map, and display the oxygen concentration map on the display device 60. Note that a monitor of the control device 40 can be used as the display device 60.

Figure 9:
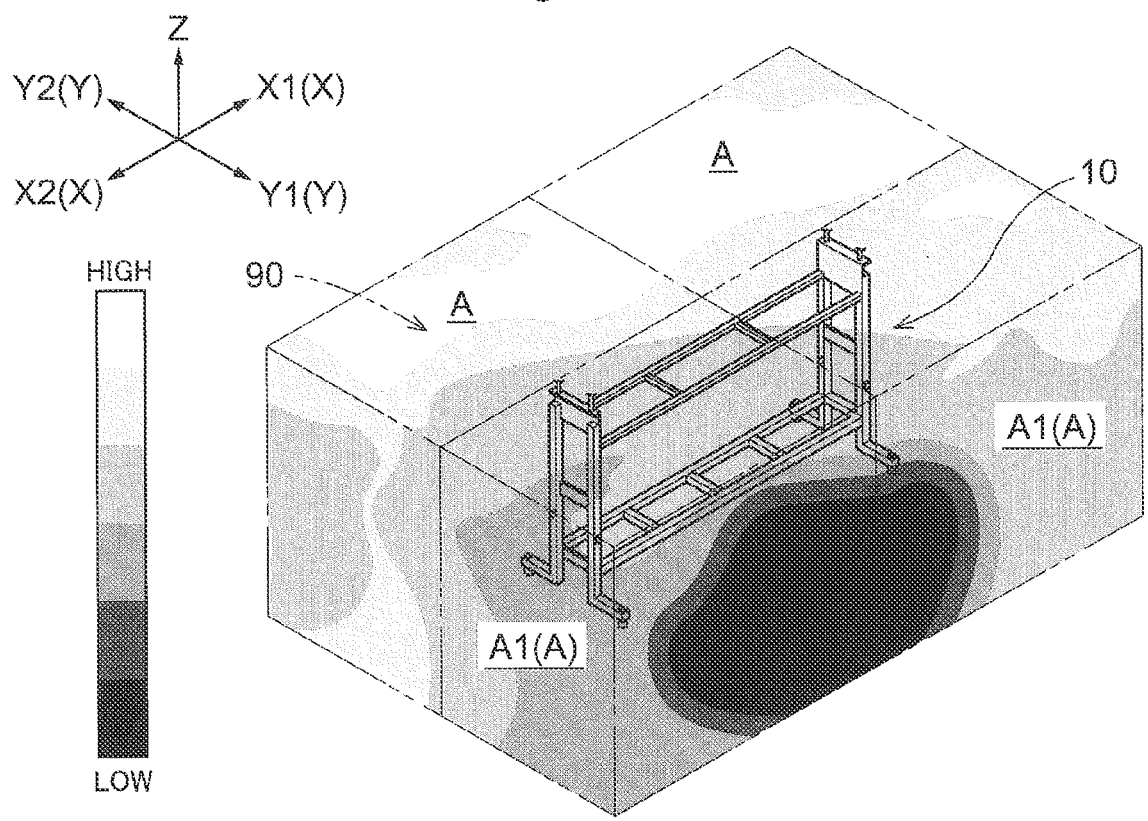
FIG. 9 shows an example of a map displayed on a display device.

FIG. 9 shows an example of the oxygen concentration map displayed on the display device 60. Such an oxygen concentration map is displayed on the display device 60, which is checked by a worker, and thus the oxygen concentrations in the storage space 90 of the container storage facility 1 can be easily visually understood. Although the scale of the oxygen concentration is divided into six levels in the example shown in FIG. 9, the scale may be divided into smaller units. To facilitate understanding by a worker who has checked the oxygen concentration map shown in FIG. 9, it is preferable that an image representing the container storage rack 10 is superposed on the oxygen concentration map. In FIG. 9, the above-described monitoring areas A in which the oxygen concentration is less than or equal to the predetermined determination threshold are shown as the low-oxygen concentration areas A1.

Figure 10:
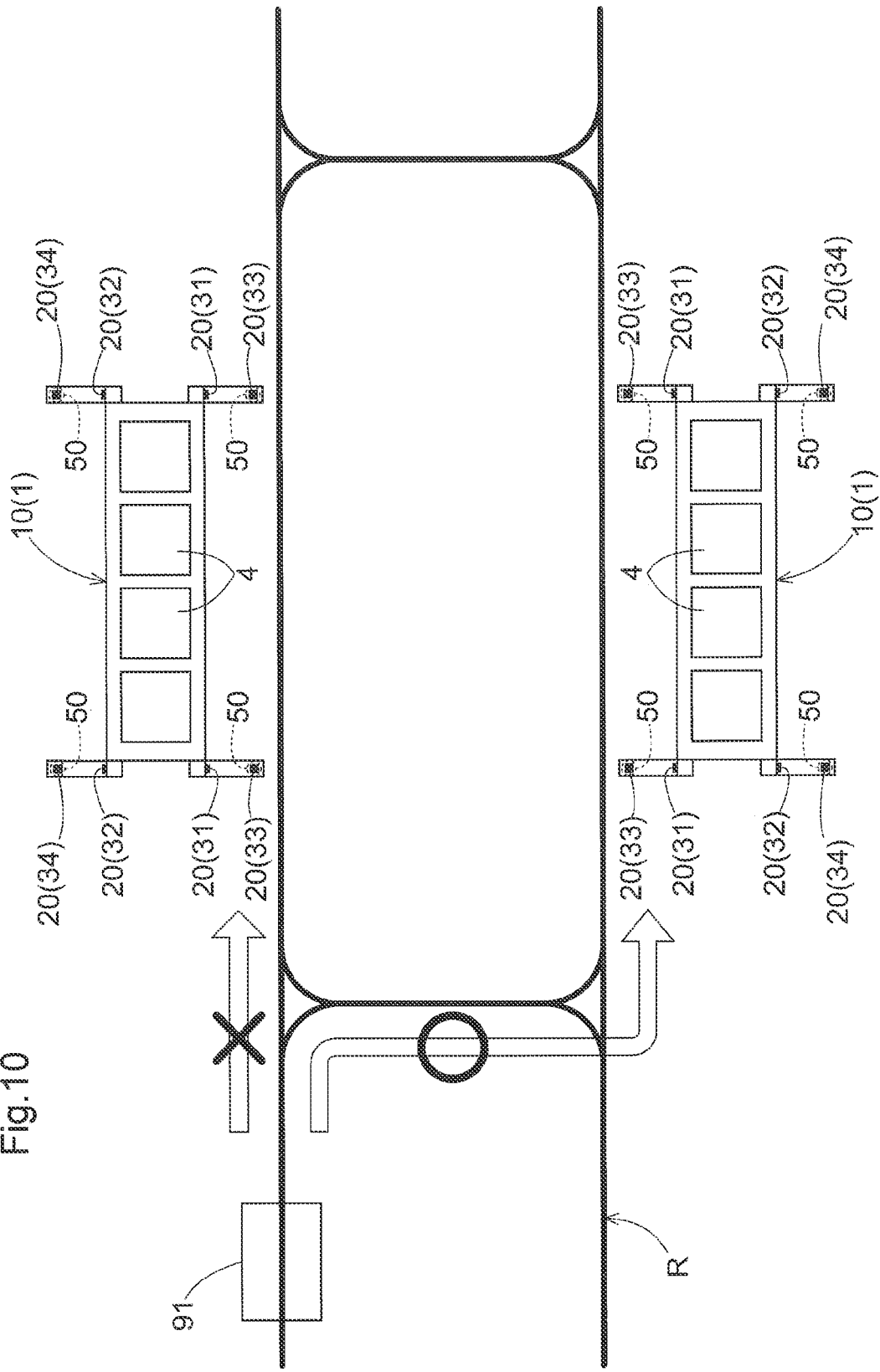
FIG. 10 is a diagram showing an article transport device that transports containers.

For example, as shown in FIG. 10, there are cases where a clean room is provided with a plurality of container storage facilities 1, and a transport device 91 that transports containers 4 by moving along a movement path R and is provided in such a manner as to connect the container storage facilities 1 to one another. For example, the transport device 91 is a transport vehicle that travels along a movement path R connecting container transfer locations serving as a transport source of the containers 4 and a transport destination of the containers 4. The container storage facilities 1 are disposed along the movement path R. In such a configuration, it is preferable that, if at least one of the plurality of monitoring areas A that are set around each of the container storage racks 10 is a low-oxygen concentration area A1, and if the corresponding human detection sensor 50 detects a person attempting to enter the low-oxygen concentration area A1, the transport device 91 is configured to not transport the containers 4 to the container storage facility 1 in which the monitoring area A that has been determined as being the low-oxygen concentration area A1 is set. In FIG. 10, "O" is assigned to a movement path to a container storage facility 1 to which the transport device 91 transports the containers 4, and "X" is assigned to a movement path to a container storage facility 1 to which the transport device 91 does not transport the containers 4. Accordingly, it is possible to prevent a person (worker) located close to the container storage facility 1 and the transport device 91 from coming into contact with each other. Furthermore, it is possible to avoid such a situation where, after a container 4 has been placed in a container storage facility 1 where a monitoring area A that is a low-oxygen concentration area A1 is set, the worker cannot approach the container 4 despite needing to.

OTHER EMBODIMENTS

Next, other embodiments of the container storage facility 1 will be described.

(1) In the above embodiment, the container storage rack 10 is described, taking, as an example, an open rack having no peripheral wall portion disposed therearound. However, the present invention is not limited to such a configuration. For example, the container storage rack 10 may be a sealed rack surrounded by a peripheral wall portion. In addition, although the container placement sections 11 are illustrated as being disposed in a single row in the present example, the container placement sections 11 may be disposed in a plurality of rows. Furthermore, the present example illustrates a configuration in which four container placement sections 11 are provided in one container storage rack 10 in such a manner as to extend in the first direction X. However, the number of container placement sections 11 may be one, or may be a plural number other than four. In such a case as well, it is possible to appropriately detect the oxygen concentrations around the container storage rack 10 by providing the container storage rack 10 with the oxygen concentration sensors 20.

(2) In the above embodiment, the control device 40 is described as being configured to output an alarm in response to at least one of the monitoring areas A being a low-oxygen concentration area A1 in which the estimated oxygen concentration is less than or equal to a predetermined determination threshold, and the human detection sensor 50 detecting a person attempting to enter the low-oxygen concentration area A1. However embodiments of the container storage facility 1 are not limited to such a configuration. For example, the control device 40 can perform control in such a manner as to cause the flow rate adjustment device 45c of the inactive gas supply apparatus 45 to reduce the flow rate of the inactive gas supplied to the container storage rack 10, or stop the supply of the inactive gas, if at least one of the monitoring areas A is a low-oxygen concentration area A1 in which the estimated oxygen concentration is less than or equal to a predetermined determination threshold. In such a case, the container storage facility 1 need not include any human detection sensor 50.

(3) The above embodiment illustrates a case where one human detection sensor 50 is provided in one monitoring area A. However embodiments of the container storage facility 1 are not limited to such a configuration. For example, one human detection sensor 50 may be provided for a plurality of monitoring areas A. In this case, one human detection sensor 50 may be configured to include detection ranges corresponding to a plurality of monitoring areas A, and detect a person attempting to enter any of the plurality of monitoring areas A. For example, one human detection sensor 50 may be provided at a central portion of the container storage rack 10 in the second direction Y on the first direction-first side X1, in place of the two human detection sensors 50 on the first direction-first side X1, and one human detection sensor 50 may be provided at a central portion of the container storage rack 10 in the second direction Y on the first direction-second side X2, in place of the two human detection sensors 50 on the first direction-second side X2. Alternatively, the container storage facility 1 need not include any human detection sensor 50.

(4) In the above embodiment, the display device 60 is described as being a monitor of the control device 40. However embodiments of the container storage facility 1 are not limited to such a configuration. The display device 60 may be a monitor of a portable terminal carried by a worker, or may be a pair of smart glasses (a display device integrated in one piece with glasses) if worn by a worker.

(5) In the above embodiment, the control device 40 is described as including the monitoring area setting unit 41, the oxygen concentration estimation unit 42, the alarm output unit 43, and the map generation unit 44. However embodiments of the container storage facility 1 are not limited to such a configuration. The functional units constituting the control device 40 are merely examples, and the grouping of the functional units can be changed as appropriate. The control device 40 can be configured to include other functional units.

(6) Note that the configurations disclosed in the embodiments described above are applicable in combination with configurations disclosed in other embodiments as long as no inconsistency arises. With regard to the other configurations as well, the embodiments disclosed herein are illustrative in all respects. Therefore, various modifications and alterations may be made as appropriate without departing from the gist of the present disclosure.

Outline of the Embodiment

In the following, an outline of the container storage facility described above will be described.

A container storage facility including:
a container storage rack including a plurality of container placement sections on each of which a container is placeable; and
an inactive gas supply apparatus configured to supply an inactive gas to each of the containers placed on the container placement sections,
wherein the container storage rack is configured to be suspended from and supported by a ceiling, and the plurality of container placement sections are next to each other in a first direction extending in a horizontal direction, and,
the container storage facility further includes:
a first sensor group including a plurality of oxygen concentration sensors at an overlapping height and next to each other in the first direction on a first side of the containers in a second direction orthogonal to the first direction as viewed in a vertical direction, the overlapping height being a position overlapping the containers placed on the container placement sections;
a second sensor group including a plurality of oxygen concentration sensors at the overlapping height and next to each other in the first direction on a second side of the containers in the second direction;
a third sensor group including a plurality of oxygen concentration sensors at a first predetermined height and next to each other in the first direction at positions further toward the first side in the second direction than the first sensor group, the first predetermined height being lower than the overlapping height; and
a fourth sensor group including a plurality of oxygen concentration sensors at a second predetermined height and next to each other in the first direction at positions further toward the second side in the second direction than the second sensor group, the second predetermined height being lower than the overlapping height.

In a container storage facility including a container storage rack including a plurality of container placement sections on each of which a container is placeable, and an inactive gas supply apparatus configured to supply an inactive gas to each of the containers placed on the container placement sections, the oxygen concentration may be locally reduced according to the extent of leakage of the inactive gas from the containers. In this case, the worker cannot enter the area in which the oxygen concentration is reduced. In particular, around a container storage rack that is suspended from and supported by a ceiling, the oxygen concentration may be locally reduced in the vicinity of the head of a worker approaching the container storage rack. In such a case, it is necessary to appropriately detect the reduction, and to alert the worker or the like. With this configuration, it is possible to appropriately detect oxygen concentrations around a container storage rack that is suspended from and supported by a ceiling, wherein the head of a worker is assumed to approach the container storage rack from below.

Here, it is preferable that the container storage facility further includes:
a control device; and
at least one human detection sensor configured to detect a person,
wherein the container storage rack, the first sensor group, the second sensor group, the third sensor group, and the fourth sensor group are located in a space divided into a plurality of monitoring areas, and the at least one human detection sensor is configured to detect presence of a person attempting to enter the monitoring areas, and
the control device is configured to (i) estimate an oxygen concentration of each of the plurality of monitoring areas based on a detection value of each of the plurality of oxygen concentration sensors constituting the first sensor group, the second sensor group, the third sensor group, and the fourth sensor group, and (ii) output an alarm in response to at least one of the monitoring areas being a low-oxygen concentration area in which the estimated oxygen concentration is less than or equal to a predetermined determination threshold, and the at least one human detection sensor detecting a person attempting to enter the low-oxygen concentration area.

With this configuration, if a worker approaches a container storage rack that is suspended from and supported by a ceiling, and the oxygen concentration in the vicinity of the head of the worker is locally reduced, it is possible to appropriately detect the reduction and output an alarm.

It is preferable that the at least one human detection sensor includes a plurality of the human detection sensors disposed in one-to-one correspondence with the plurality of monitoring areas.

With this configuration, it is possible to appropriately detect the presence of a person entering each of the plurality of monitoring areas.

It is preferable that the control device is configured to, based on detection values of all the oxygen concentration sensors constituting the first sensor group, the second sensor group, the third sensor group, and the fourth sensor group, estimate a minimum value of the oxygen concentration of each of the plurality of monitoring areas through spatial interpolation, and determine each of the monitoring areas for which the minimum value is less than or equal to the determination threshold to be the low-oxygen concentration area.

With this configuration, even if the number of oxygen concentration sensors disposed in the periphery of the container storage rack is relatively small, it is possible to accurately determine whether or not there is a low-oxygen concentration area.

It is preferable that the container storage facility further includes a display device,
wherein the control device is configured to display, on the display device, an oxygen concentration estimated for each of the plurality of monitoring areas as an oxygen concentration map associated with a location of the container storage rack.

With this configuration, the oxygen concentration is estimated for each of the plurality of monitoring areas obtained by dividing the area surrounding the container storage rack, and the result of estimation is displayed as an oxygen concentration map on the display device. Accordingly, it is possible to inform a worker of the oxygen concentration at each location around the container storage rack in an easily understandable manner.

INDUSTRIAL APPLICABILITY

The technique according to the present disclosure is applicable to a container storage facility including a container storage rack including a plurality of container placement sections on each of which a container is placeable, and an inactive gas supply apparatus configured to supply an inactive gas to each of the containers placed on the container placement sections.

What is claimed is:

1. A container storage facility comprising:
   a container storage rack comprising a plurality of container placement sections on each of which a container is placeable; and
   an inactive gas supply apparatus configured to supply an inactive gas to each of the containers placed on the container placement sections,
   wherein the container storage rack is configured to be suspended from and supported by a ceiling, and the plurality of container placement sections are next to each other in a first direction extending in a horizontal direction, and,
   the container storage facility further comprises:
   a first sensor group comprising a plurality of oxygen concentration sensors at an overlapping height and next to each other in the first direction on a first side of the containers in a second direction orthogonal to the first direction as viewed in a vertical direction, the overlapping height being a position overlapping the containers placed on the container placement sections;
   a second sensor group comprising a plurality of oxygen concentration sensors at the overlapping height and next to each other in the first direction on a second side of the containers in the second direction;
   a third sensor group comprising a plurality of oxygen concentration sensors at a first predetermined height and next to each other in the first direction at positions further toward the first side in the second direction than the first sensor group, the first predetermined height being lower than the overlapping height; and
   a fourth sensor group comprising a plurality of oxygen concentration sensors at a second predetermined height and next to each other in the first direction at positions further toward the second side in the second direction than the second sensor group, the second predetermined height being lower than the overlapping height.

2. The container storage facility according to claim 1, further comprising:
   a control device; and
   at least one human detection sensor configured to detect a person,
   wherein the container storage rack, the first sensor group, the second sensor group, the third sensor group, and the fourth sensor group are located in a space divided into a plurality of monitoring areas, and the at least one human detection sensor is configured to detect presence of a person attempting to enter the monitoring areas, and
   the control device is configured to (i) estimate an oxygen concentration of each of the plurality of monitoring areas based on a detection value of each of the plurality of oxygen concentration sensors constituting the first sensor group, the second sensor group, the third sensor group, and the fourth sensor group, and (ii) output an alarm in response to at least one of the monitoring areas being a low-oxygen concentration area in which the estimated oxygen concentration is less than or equal to a predetermined determination threshold, and the at least one human detection sensor detecting a person attempting to enter the low-oxygen concentration area.

3. The container storage facility according to claim 2, wherein the at least one human detection sensor comprises a plurality of the human detection sensors disposed in one-to-one correspondence with the plurality of monitoring areas.

4. The container storage facility according to claim 2, wherein the control device is configured to, based on detection values of all the oxygen concentration sensors constituting the first sensor group, the second sensor group, the third sensor group, and the fourth sensor group, estimate a minimum value of the oxygen concentration of each of the plurality of monitoring areas through spatial interpolation, and determine each of the monitoring areas for which the minimum value is less than or equal to the determination threshold to be the low-oxygen concentration area.

5. The container storage facility according to claim 2, further comprising a display device,
wherein the control device is configured to display, on the display device, an oxygen concentration estimated for each of the plurality of monitoring areas as an oxygen concentration map associated with a location of the container storage rack.

* * * * *